US010550361B2

(12) United States Patent
Köll (10) Patent No.: US 10,550,361 B2
(45) Date of Patent: Feb. 4, 2020

(54) HINGEDLY SUPPORTED BIOGAS PLANT FERMENTATION CONTAINER

(71) Applicant: Thöni Industriebetriebe GmbH, Telfs (AT)

(72) Inventor: Thomas Köll, Telfs (AT)

(73) Assignee: THÖNI INDUSTRIEBETRIEBE GMBH, Telfs (AT)

( * ) Notice: Subject to any disclaimer, the term of this patent is extended or adjusted under 35 U.S.C. 154(b) by 0 days.

(21) Appl. No.: 15/737,441

(22) PCT Filed: Jun. 19, 2015

(86) PCT No.: PCT/EP2015/063859
§ 371 (c)(1),
(2) Date: Dec. 18, 2017

(87) PCT Pub. No.: WO2016/202407
PCT Pub. Date: Dec. 22, 2016

(65) Prior Publication Data
US 2018/0112169 A1    Apr. 26, 2018

(51) Int. Cl.
*C12M 3/00* (2006.01)
*C12M 1/107* (2006.01)

(52) U.S. Cl.
CPC ............ *C12M 23/48* (2013.01); *C12M 21/04* (2013.01)

(58) Field of Classification Search
CPC .............................. C12M 27/16; C12M 23/48

USPC ....................................................... 435/305.1
See application file for complete search history.

(56) References Cited

U.S. PATENT DOCUMENTS 4,264,741 A * 4/1981 Friedman ............... C12M 27/06
366/234

FOREIGN PATENT DOCUMENTS

| CN | 102 851 204 A | 1/2013 |
| DE | 10 2010 008897 A1 | 8/2011 |
| EP | 2 561 925 A1 | 2/2013 |
| EP | 2 562 241 A1 | 2/2013 |
| EP | 2 562 242 A1 | 2/2013 |
| EP | 2 562 243 A1 | 2/2013 |
| EP | 2 561 925 B1 | 2/2014 |

* cited by examiner

*Primary Examiner* — Kevin Joyner
*Assistant Examiner* — Holly M Mull
(74) *Attorney, Agent, or Firm* — Robert A. Blaha; Smith Tempel Blaha LLC (57) ABSTRACT

A biogas plant is provided comprising a fermentation container for receiving fermentation material to be fermented. The fermentation container comprises a lower wall part and an upper wall part where the upper wall part is positioned above the lower wall part. Further, the biogas plant comprises a support and a hinge wherein the hinge hingedly connects the fermentation container to the support and wherein the hinge defines a pivot axis about which the upper wall part and the lower wall part are pivotable.

18 Claims, 3 Drawing Sheets

HINGEDLY SUPPORTED BIOGAS PLANT FERMENTATION CONTAINER

CROSS-REFERENCE TO RELATED APPLICATION

This application is a national phase application, which is derived from international patent application number PCT/EP2015/063859, filed on Jun. 19, 2015, the disclosure of which is hereby incorporated by reference in its entirety.

TECHNICAL FIELD

The present invention relates to the field of biogas plants.

TECHNOLOGICAL BACKGROUND

From practice, biogas plants with fermentation containers made of concrete and fermentation containers made of steel are known.

Further, from EP 2562241 A1 there is known a fermenter comprising a wall and a preshaped bottom element defining the contour of an inner bottom surface of the fermenter. The preshaped bottom element has an outer surface portion, the outer surface portion facing the wall and being laterally spaced from a lower part of the wall. A coupling element comprises a first portion which is attached to an attachment surface of the preshaped bottom element and further comprises a second portion which is coupled to the wall of the fermenter. The fermenter may comprise a support wherein the preshaped bottom element has a bearing face resting on the support. The support may extend from the bearing face to the ground plate. The bearing face may have a curved shape and the support may have a respectively formed opposing shape such that the preshaped bottom element is pivotable with respect to the support. Such a configuration, wherein the bearing face and the opposing face on the support provide for the preshaped bottom element being pivotable with respect to the support, can reduce shearing forces on the support.

SUMMARY

Conventional fermentation containers have the disadvantage that large fermentation containers require thick sidewalls to bear high hydrostatic pressure in the fermentation container e.g. a pressure arising from a hydrostatic column of fermentation material with a height of 5 to 15 meters (m).

In view of the above-described situation, there exists a need for an improved technique that enables to provide a fermentation container, while substantially avoiding or at least reducing one or more of the above-identified problems.

This need may be met by the subject matter according to the independent claims. Advantageous embodiments of the herein disclosed subject matter are described by the dependent claims.

In the following, exemplary embodiments of the herein disclosed subject matter are described. Any number and any combination of embodiments may be realized in an implementation of the herein disclosed subject matter.

According to a first aspect of the herein disclosed subject matter there is provided a biogas plant comprising: a fermentation container for receiving fermentation material to be fermented, the fermentation container comprising a lower wall part and an upper wall part, the upper wall part being positioned above the lower wall part; a support; and a hinge, the hinge hingedly connecting the fermentation container to the support, the hinge defining a pivot axis about which the upper wall part and the lower wall part are pivotable.

This aspect is based on the idea that by hingedly connecting the fermentation container to the support improves the load characteristics on the support. By improving the load characteristics on the support, the support may be manufactured with a lower rated load or may be subject to lower lateral forces.

According to an embodiment, the hinge provides for a movability of the fermentation container with respect to the support lengthwise (e.g. parallel to) the pivot axis. In this way, stresses due to thermal expansion can be reduced.

According to an embodiment, the biogas plant and in particular the fermentation container thereof is configured for dry fermentation (e.g. dry substance content of about 30%). For example, according to an embodiment the fermentation container is a container of a plug flow fermenter.

According to an embodiment, the hinge is provided to reduce an influence of a deformation of the fermentation container on the support, e.g. during the filling of the fermentation container or due to temperature variations.

According to an embodiment, the lower wall part is spaced from the pivot axis in a direction from the support towards the fermentation container, i.e. in a lateral direction. Hence, a connection part bridging the spacing between the lower wall part and the pivot axis forms a lever which influences the magnitude of the torque on the upper wall part which is exerted by the lower wall part under the action of the hydrostatic pressure and weight of the fermentation material in the fermentation container. This torque on the upper wall part may counteract (e.g. at least partially balance) the hydrostatic pressure exerted by the fermentation material on the upper wall part. Since the hydrostatic pressure in the fermentation material at a certain position depends on the liquid column above that position the hydrostatic pressure exerted on the lower wall part is higher than the hydrostatic pressure exerted on the upper wall part. It should be understood that besides the hydrostatic pressure also other parameters influence the torque exerted by the lower wall part. For example, the stiffness of the lower wall part may be such a parameter. In particular, in an embodiment where the lower wall part forms at least part of a bottom of the fermentation container, a change in the shape of the bottom may also result in a torque exerted by the lower wall part.

According to an embodiment, the lower wall part is exerting to the hinge a torque in a direction pivoting the upper wall part towards an interior of the fermentation container, i.e. the lower wall part exerts an inwardly directed torque on the upper wall part. Exerting to the hinge the torque in this direction does not necessarily mean that the upper wall part is in fact pivoted towards an interior of the fermentation container. In particular, in a fully filled state of the fermentation container, wherein the fermentation material is filled up to a rated level, the configuration of the fermentation container and the hinge may be such that an outwardly directed torque on the upper wall part exerted by the fermentation material is partially compensating, fully compensating or overcompensating the inwardly directed torque exerted by the lower wall part.

According to an embodiment, the lower wall part extends at an angle with regard to the direction of gravity. For example, according to an embodiment the lower wall part extends towards a vertical middle plane of the fermentation container. According to an embodiment, the lower wall part is part of the bottom of the fermentation container. According to an embodiment, the bottom of the fermentation container is curved. According to an embodiment, the stiffness of the bottom of the fermentation container is configured such that the cross section of the bottom changes during the filling of fermentation material into the fermentation container. For example, in an empty state the cross section of the bottom of the fermentation container may be a shape of a segment of a circle which changes towards a chain line upon increasing the fill level of fermentation material.

According to an embodiment, in a filled state (e.g. in a state, in which the fermentation material in the fermentation container is filled up to a rated level), a central part of a bottom of the fermentation container is vertically moveable. In particular, according to an embodiment, the support and the fermentation container are configured such that the central part of the bottom of the fermentation container is vertically moveable if the fermentation container is filled with fermentation material up to the rated level. According to an embodiment, the support and the fermentation container are configured such that the central part of the bottom of the fermentation container rests on a middle support if the fermentation container is partially filled.

According to an embodiment, the fermentation container comprises a connection part; the connection part being connected to the lower wall part; the connection part being connected to the upper wall part; the hinge comprising a first bearing part; the hinge comprising a second bearing part at the connection part, the second bearing part cooperating with the first bearing part and being moveable with respect to the first bearing part. According to an embodiment, the first bearing part is mounted to the support.

According to a further embodiment, at least one of the first bearing part and the second bearing part have a segmented surface with a plurality of edges. For example, according to an embodiment the segmented surface comprises flat segments joined at an angle to form the edges. For example, in an embodiment the segmented surface is formed from sheet metal, e.g. by polygonally bent sheet metal, or in another embodiment, by at least two pieces of sheet metal which are attached to each other side by side, e.g. by welding, thereby forming a cross section of the respective bearing part. Such an embodiment allows for a cost efficient manufacture of the respective bearing part. The thickness of the sheet metal used is generally adapted to the specific purpose and dimensions of the fermentation container. For example, for the polygonally bent sheet metal of a bearing part, the thickness may be in a range between 3 millimeters (mm) and 15 mm. For instance, the thickness of the sheet metal may be 10 mm.

According to an embodiment, the hinge further comprises a slideway lining between the first bearing part and the second bearing part, the slideway lining being in particular made of plastic material. The slideway lining improves the sliding movability of the first bearing part and the second bearing part with regard to each other. Further, the slideway lining may compensate manufacturing tolerances of the first bearing part and/or the second bearing part. Further, the slideway lining may provide for movability of bearing parts having a segmented surface.

According to an embodiment, the material of the slideway lining is subject to creep; and the hinge further comprises a closed lining chamber comprising the slideway lining, the lining chamber being at least partially defined by the first bearing part and the second bearing part. The closed lining chamber has the advantage that a creep of the slideway lining and does not lead to a substantial loss of slideway lining between the first bearing part and the second bearing part and hence to a loss of the sliding properties of the hinge.

According to a further embodiment, the slideway lining has an elastic modulus which is lower that the elastic modulus of a bearing material from which at least one of the first bearing part and the second bearing part is formed. For example, according to an embodiment, the elastic modulus of the slideway lining is at least 50% lower than the elastic modulus of the bearing material. The lower elastic modulus of the slideway lining provides for an immediate deformation of the slideway lining upon a change of the forces acting on the slideway lining, e.g. during filling the fermentation container with fermentation material. Thus providing an advantageous force distribution between the first bearing part and the second bearing part is achieved even on short time scales during which no relevant creep of the slideway lining occurs.

According to a further embodiment, the slideway lining has a coefficient of thermal conduction which is lower than the coefficient of thermal conduction of the bearing material. This reduces the heat transfer over the hinge, i.e. the heat transfer between the first bearing part and the second bearing part. This may reduce the heating up of the first bearing part and hence differences between the coefficient of thermal expansion of the first bearing part and the support are of less relevance. Further this may lead to a reduced temperature gradient in the support and to reduced stresses in the support, in particular if the support is, in accordance with an embodiment, made of concrete.

According to a further embodiment, the biogas plant further comprises a position adjustment device allowing for adjustment of a position of the first bearing part with respect to the support. For example, according to an embodiment the position adjustment device allows the adjustment of the vertical position of the first bearing part with respect to the support. In such a case the position of the first bearing part can be adjusted to level out variations in the height of the support or a slope of the support. According to a further embodiment, the position adjustment device allows the adjustment of the horizontal position of the first bearing part with respect to the support. For example in such a case lateral manufacturing tolerances of the support may be levelled out. In accordance with an embodiment, the position adjustment device allows for a precise adjustment of the position and/or the alignment of the first bearing part before the second bearing part and the fermentation container is mounted to the first bearing part.

According to an embodiment, the biogas plant further comprises a grouting material (e.g. a grouting compound) in a space between the first bearing part and the support. The grouting material may provide for a force transfer between the first bearing part and the support. This allows a construction of the first bearing part which is not capable of bearing the entire load of the fermentation container but needs support from below in order to bear the fermentation container with the fermentation material. Hence, the first bearing part can be lighter which facilitates adjustment of the position and/or alignment of the first bearing part. According to an embodiment, the grouting material is a grouting mortar. The grouting material may be omitted if omitting the grouting material is compensated with appropriate dimensions of the first bearing part (i.e. if the first bearing part is adapted to bear and transfer the force exerted on the first bearing part during operation of the fermentation device, in particular the force exerted by the fermentation container, to the support or an intermediate part (e.g. a position adjustment device) to which the first bearing part is mounted). It should be understood that if a position adjustment device is used, also the position adjustment device is adapted to bear and transfer the force exerted on the position adjustment device (during operation of the fermentation device) to the support.

According to an embodiment, the hinge extends over at least 80 percent (e.g. 90 percent, 95 percent or 100 percent) of the entire length of the fermentation container. However, in a further embodiment the hinge may extend beyond the fermentation container. For example, in an embodiment where the fermentation container has a substantially rectangular layout (cross section when viewed from above) the hinge may extend over at least 80 percent of the entire length of the longest side of the fermentation container.

According to an embodiment, the support is a wall, in particular a concrete wall (e.g. a reinforced concrete wall), extending lengthwise the fermentation container.

According to a further embodiment, the location of the fermentation container with respect to the support is fixed in a direction along the pivot axis. For example, in an embodiment the hinge is configured so as to fix the location of the fermentation container with respect to the support in a direction along the pivot axis.

According to an embodiment, the fermentation container is made of metal. Making the fermentation container from metal has the advantage that the fermentation container and in particular the bottom of the fermentation container can be constructed so as to be deformable under load of the fermentation material in the fermentation container, thereby supporting advantageous torque distributions in accordance with embodiments of the herein disclosed subject matter. In particular the bottom of the fermentation container made of metal is, according to an embodiment, configured to be supported only by the hinge.

According to an embodiment, the shape of the fermentation container is configured and the hinge is configured and located such that above a first level of fermentation material an increase of the level of fermentation material in the fermentation container increases an outwardly directed force acting on the support in a direction away from the fermentation container. According to a further embodiment, below the first level of fermentation material an increase of the level of fermentation material increases an inwardly directed force acting on the support in a direction towards the fermentation container.

According to an embodiment, a roof of the fermentation container is abutting an upper wall part. The roof may be made of any suitable type, e.g. may be made of steel.

According to an embodiment, the biogas plant comprises two or more hinges by each of which the fermentation container is hingedly connected to a respective support. For example, according to an embodiment, the support is a first support, the hinge is a first hinge, the lower wall part is a first lower wall part, the upper wall part is a first upper wall part, and the pivot axis is a first pivot axis, the fermentation container further comprises a second lower wall part and a second upper wall part, and the biogas plant further comprises: a second support spaced from the first support, wherein the fermentation container is located between the first support and the second support; a second hinge for hingedly connecting the fermentation container to the second support, the second hinge defining a second pivot axis about which the second lower wall part and the second upper wall part are pivotable.

According to an embodiment, the fermentation container is symmetrical with regard to a middle plane. According to a further embodiment, the first support and the second support are symmetrical with regard to the middle plane.

According to embodiments of the first aspect, the biogas plant is adapted for providing the functionality of one or more of the embodiments disclosed herein and/or for providing the functionality as required by one or more of the embodiments herein, in particular of the embodiments of a second aspect discussed below.

According to a second aspect of the herein disclosed subject matter, a method of constructing a biogas plant is provided, wherein the biogas plant comprises a fermentation container being provided for receiving fermentation material to be fermented, the fermentation container comprising a lower wall part and an upper wall part being positioned above the lower wall part, the method comprising: providing a support; hingedly connecting the fermentation container to the support by a hinge, the hinge defining a pivot axis about which the upper wall part and the lower wall part are pivotable.

According to an embodiment, wherein the hinge comprises a first bearing part and a second bearing part, and the method comprises: locating the first bearing part on the support; adjusting a position of the first bearing part with respect to the support; positioning the second bearing part on the first bearing part.

According to an embodiment, adjusting the position of the first bearing part with respect to the support comprises adjusting the vertical position of the first bearing part with respect to the support. According to another embodiment, adjusting the position of the first bearing part with respect to the support comprises adjusting the horizontal position of the first bearing part with respect to the support.

According to an embodiment, the method further comprises at least one of the following: providing a bottom bearing which limits the downward movement of the central-lower part of the bottom of the fermentation container; connecting pieces of the fermentation container to thereby generate a segment, the segment forming at least part of the entire cross profile of the fermentation container, the segment extending over a part of a length of the fermentation container; mounting the segment to the bottom bearing and the first bearing part; connecting the segment of the fermentation container with an adjacent segment to thereby build up the fermentation container. According to an embodiment, the segment is adapted for being mounted to the bottom bearing and the first bearing part. In other words, in this embodiment, the segment is adapted for extending between the bottom bearing and the first bearing part.

According to a further embodiment, the method further comprises the order: providing a base plate; providing the support and the bottom bearing on the base plate; providing the first bearing part on the support and providing the second bearing part on the segment; mounting the segment to the first bearing part and the bottom bearing.

According to embodiments of the second aspect, the method is adapted for providing the functionality of one or more of the embodiments disclosed herein and/or for providing the functionality as required by one or more of the embodiments disclosed herein, in particular of the embodiments of the first aspect.

In the above there have been described and in the following there will be described exemplary embodiments of the subject matter disclosed herein with reference to a biogas plant and respective methods for constructing the same. It has to be pointed out that of course any combination of features relating to the same aspect or relating to different aspects of the herein disclosed subject matter is possible. In particular, some features have been or will be described with reference to apparatus type embodiments whereas other features have been or will be described with reference to method type embodiments. However, a person skilled in the art will gather from the above and the following description that, unless otherwise notified, in addition to any combination of features belonging to one aspect also any combination of features relating to different aspects or embodiments, for example even combinations of features of apparatus type embodiments and features of the method type embodiments are considered to be disclosed with this application. In this regard, it should be understood that any device type feature is intended to implicitly disclose a respective method type feature based on the respective function of the device feature. In this regard, the method type feature or function shall not be considered as being limited to device specific elements disclosed in conjunction with the device type feature.

The aspects and embodiments defined above and further aspects and embodiments of the herein disclosed subject matter are apparent from the examples to be described hereinafter and are explained with reference to the drawings, but to which the invention is not limited.

DETAILED DESCRIPTION OF ILLUSTRATED EMBODIMENTS

The illustration in the drawings is schematic. It is noted that even in different figures, similar or identical elements are provided with the same reference signs or with reference signs which are different from the corresponding reference signs only with the first digit. Accordingly, the description of similar or identical features is not repeated in the description of subsequent figures in order to avoid unnecessary repetitions. However, it should be understood that the description of these features in the preceding figures is also valid for the subsequent figures unless noted otherwise.

Figure 1:
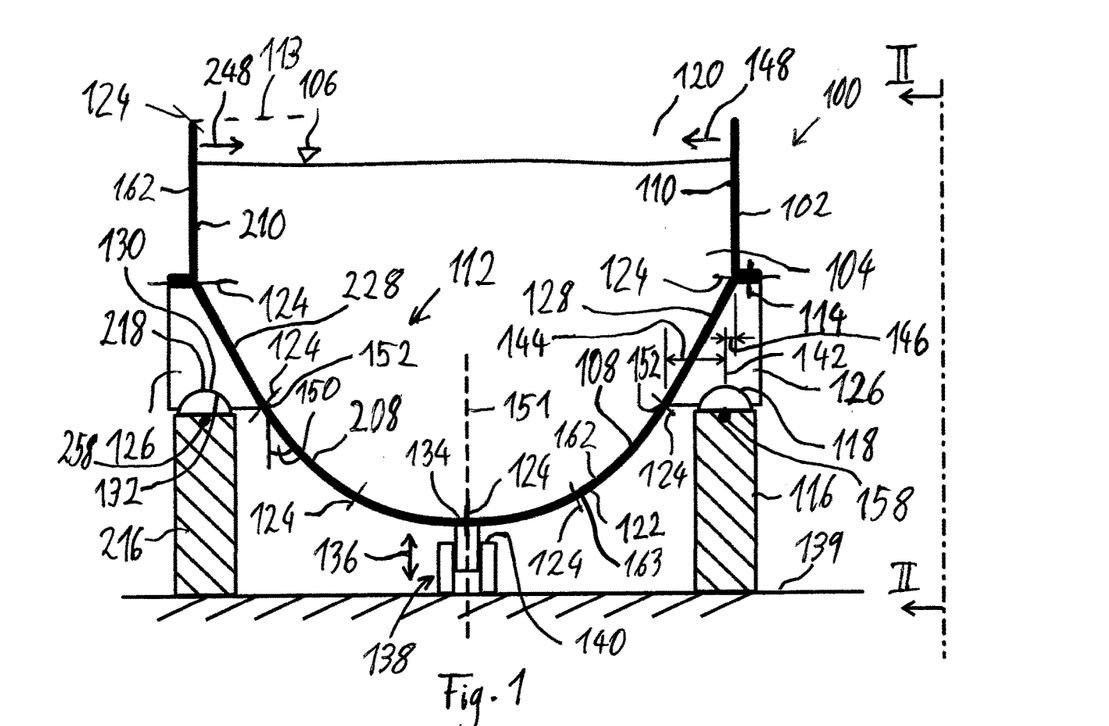
FIG. 1 shows part of a biogas plant according to embodiments of the herein disclosed subject matter.

FIG. 1 shows part of a biogas plant 100 according to embodiments of the herein disclosed subject matter.

The biogas plant 100 comprises a fermentation container 102 for receiving fermentation material 104. According to an embodiment, the fermentation container 102 is configured for being filled with fermentation material 104 up to a rated level 106. According to an embodiment, a stirring device (not shown in FIG. 1) is located in the fermentation container 102 for stirring the fermentation material 104. The fermentation container 102 comprises a first lower wall part 108 and a first upper wall part 110. The first upper wall part 100 is located above the first lower wall part 108.

The biogas plant 100 comprises a first support 116 and a first hinge 118 which hingedly connects the fermentation container 102 to the first support 116. The first hinge 118 defines a first pivot axis 158 about which the first upper wall part 110 and the first lower wall part 108 are pivotable.

In accordance with an embodiment, the fermentation container 102 comprises a second lower wall part 208 and a second upper wall part 210. According to an embodiment, the first upper wall part 110, the first lower wall part 108, the second lower wall part 208 and the second upper wall part 210 are part of an entire cross profile 112 of the fermentation container 102. In this regard it is noted that the fermentation container 102 comprises a roof 113 (schematically shown in part in FIG. 1, e.g. a solid roof or a plastic sheet roof) in order to provide a closed space 120 in which a biogas, produced from fermentation of the fermentation material 104, is collected. According to an embodiment, the lower wall part 108, 208 forms at least part of a bottom 122 of the fermentation container 102. According to an embodiment, the bottom 122 of the fermentation container 102 is formed by the first lower wall part 108 and the second lower wall part 208. According to an embodiment, the upper wall part 110, 210 extends up to the rated level 106.

The biogas plant comprises a second support 216 and a second hinge 218 which hingedly connects the fermentation container 102 to the second support 216. The second hinge 218 defines a second pivot axis 258 about which the second upper wall part 210 and the second lower wall part 208 are pivotable. According to an embodiment, the first pivot axis 158 and the second pivot axis 258 are parallel, as is the case for the biogas plant 100 shown in FIG. 1. According to an embodiment, the first support 116 and the second support 216 is a lateral and vertical support of the fermentation container 102. According to an embodiment, the vertical force component is higher than the horizontal (lateral) force component acting on the support 116, 216.

According to an embodiment, the entire cross profile 112 (which may or may not include the roof 113) of the fermentation container 102 is formed of several individual pieces (some of which are shown in FIG. 1 at 162) in order to facilitate assembly of the fermentation container 102, in particular for large fermentation containers having e.g. a volume above 500 m³. Exemplary positions of joints of individual pieces 162 are indicated by the lines 124 in FIG. 1. The individual pieces 162 may be attached to each other by suitable attachment elements such as bolts 114, weld lines (not shown in FIG. 1), etc. For example, in large fermentation containers construction may be facilitated by providing two or more individual pieces 162 for constructing the lower wall part 108 and the upper wall part 110. The extent of the individual pieces 162 may or may not correspond to the wall parts 108, 110, 208, 210. In other words, although possible according to an embodiment the upper and lower wall parts do not necessarily define individual pieces 162 from which the fermentation container is manufactured but rather define regions of the fermentation container providing features and functions as disclosed herein.

According to an embodiment, a segment 163 of the fermentation container is built by two or more pieces 162. The segment 163 forms at least part of the entire cross profile 112 of the fermentation container 102. For example, in an embodiment, the segment 163 forms half of the bottom 122 and is mounted to the bottom bearing 138 and the first bearing part 130. For example, according to an embodiment, the segment 163 includes connection part 126. Adjacent segments (e.g. a segment forming the upper wall part 110, and laterally adjacent segment not shown in FIG. 1) are connected to thereby build up the entire fermentation container 102.

According to an embodiment, the fermentation container comprises a connection part 126 which is connected to the neighboring lower wall part 108, 208 and the neighboring upper wall part 110, 210. According to an embodiment, the connection part 126 comprises an intermediate wall part 128, 228 which extends between the lower wall part 108, 208 and the upper wall part 110, 210. According to an embodiment, the intermediate wall part 128, 228 is formed by an individual piece of the entire cross profile 112, is attached to the connection part 126 and may be provided together with the connection part 126 as a pre-manufactured subassembly.

According to an embodiment, the hinge 118, 218 comprises a first bearing part 130 and a second bearing part 132 configured for cooperating with the first bearing part 130 and being movable with respect to the first bearing part 130.

According to an embodiment, the bottom 122—at least in a filled state of the fermentation container 102—is only supported by the first support 116 and the second support 216 via the hinged connection (i.e. via hinges 118, 218). This allows for a simpler construction of the fermentation container and the support for the fermentation container. According to an embodiment, the bottom 122 is deformable so as to allow the bottom to adapt its shape to the changing forces during the filling of the fermentation container or in response to external forces resulting from temperature variations, earthquakes, etc.

According to an embodiment, in a filled state a central-lower part 134 of the bottom 122 (e.g. a container base) of the fermentation container 102 is vertically movable, i.e. is moveable in a vertical direction 136. According to an embodiment, the biogas plant comprises a bottom bearing 138 supporting the bottom 122, e.g. in the central-lower part 134 of the bottom 122. In accordance with an embodiment, the bottom bearing 138 is located on a base plate 139 on which also the first support 116 and the second support 216 are located. According to an embodiment, the bottom bearing 138 allows for a vertical movement of the central-lower part 134 of the bottom 122 of the fermentation container but limits lateral movement perpendicular to the vertical movement. According to an embodiment, the bottom bearing 138 comprises a stop face 140 which limits the downward movement of the central-lower part 134 of the bottom 122 of the fermentation container. In this way, upon filling the fermentation container 102 with fermentation material 104, the deformation of the bottom 122 of the fermentation container 102 is limited. This may be in particular helpful in early filling stages where the fermentation material is concentrated in the central lower part of the fermentation container 102.

According to an embodiment, a deflection of the bottom bearing 138 under the load of the fermentation container 102 is accounted for (e.g. is counteracted) when mounting the bottom bearing to the base plate 139. For instance, in an embodiment where the bottom bearing 138 comprises metal bars which are attached to the base plate 139, spacer elements (not shown in FIG. 1) may be located between the metal bars and the base plate 139 during mounting of the bottom bearing 138.

According to an embodiment, the lower wall part 108, 208 is spaced from the pivot axis 158, 258 and hence from a center 142 of the bearing 118, 218 in a direction from the support 116, 216 to the fermentation container 102, according to an embodiment at least by a first distance 144 as shown in FIG. 1. According to a further embodiment, the upper wall part 110, 210 is spaced from the pivot axis 158, 258 (and hence from the center 142 of the bearing 118, 218) in a direction from the fermentation container 102 to the respective support 116, 216, according to an embodiment at least by a second distance 146, as shown in FIG. 1. Hence, in accordance with an embodiment the lower wall part 108, 208 exerts to the hinge 118, 218 a torque in a direction 148, 248 pivoting the upper wall part 110, 210 towards an interior of the fermentation container 102.

According to a further embodiment, the lower wall part 108, 208 extends at an angle 150 with regard to the direction of gravity, as shown in FIG. 1. In other words, the lower wall part 108, 208 extends towards a vertical middle plane 151 of the fermentation container. According to a further embodiment, the angle 150 changes with the distance from the support 116, 216, thereby resulting in a curved lower wall part 108, 208. According to an embodiment, at a point of connection 152 in which the bottom 122 is connected to the connection part 126, the angle 150 corresponds to the direction of the tangential force on the bottom 122 in the point of connection. In other words, according to an embodiment in the point of connection 152 the angle 150 is chosen such that the connection force is within the bottom 122 and no bending forces act on the connection part 126 in the point of connection 152, at least if the fermentation container 102 is filled up to the rated level of 106.

According to an embodiment, the first distance 144, the second distance 146 and the configuration of the fermentation container, in particular of the bottom 122 of the fermentation container is such that the counteracting torques exerted by the lower wall part 108, 208 and the upper wall part 110, 210 on the hinge 118, 218 at least partially cancel each other. This may lead to reduced lateral forces on the support 116, 216. Reduced lateral forces on the support allows to reduce the dimensions of the support 116, 216 thereby providing a cost efficient biogas plant.

Figure 2:
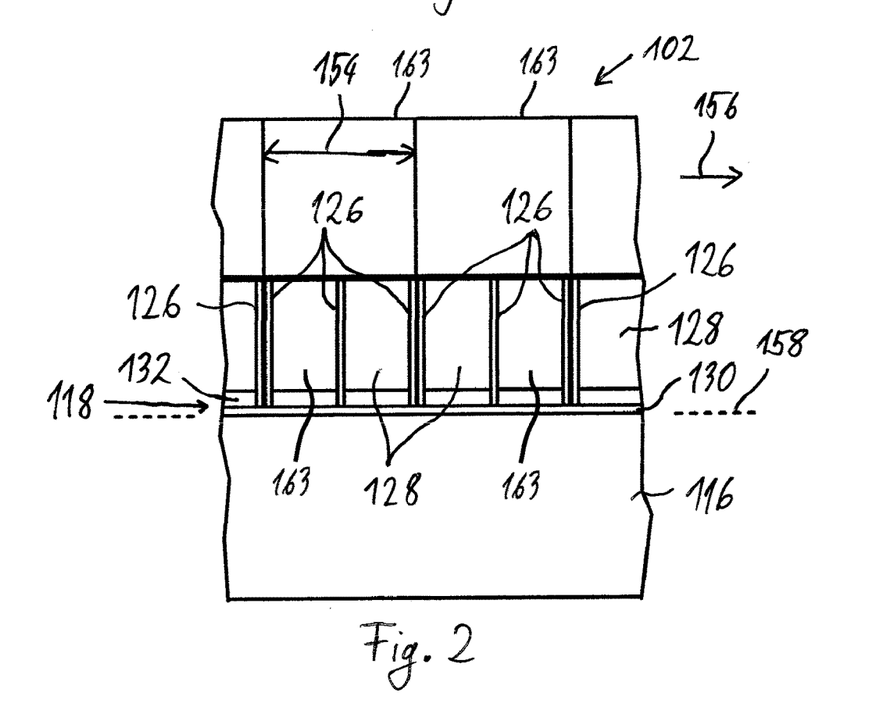
FIG. 2 shows the fermentation container of FIG. 1 in a side view, viewed along line II-II in FIG. 1.

FIG. 2 shows the fermentation container 102 of FIG. 1 in a side view, viewed along line II-II in FIG. 1.

In particular, FIG. 2 shows the backside of the intermediate wall part 128 as well as the connection parts 126. In accordance with an embodiment, the first bearing part 130 and the second bearing part 132 each extend over the entire length of the hinge 118 while the connection parts 126 are provided at certain distances. In accordance with an embodiment, the fermentation container 102 is provided in segments 163 which extend over a length 154 in axial direction 156 which is only a fraction of the entire length (not shown in FIG. 2) of the fermentation container 102. Providing the segments 163 of a suitable size allows for easier handling (e.g. easier transportation and transportation in an ISO container) of the parts of the fermentation container that form the entire cross profile 112. According to an embodiment, the axial direction 156 is parallel to the pivot axis 158 of the hinge 118.

Figure 3:
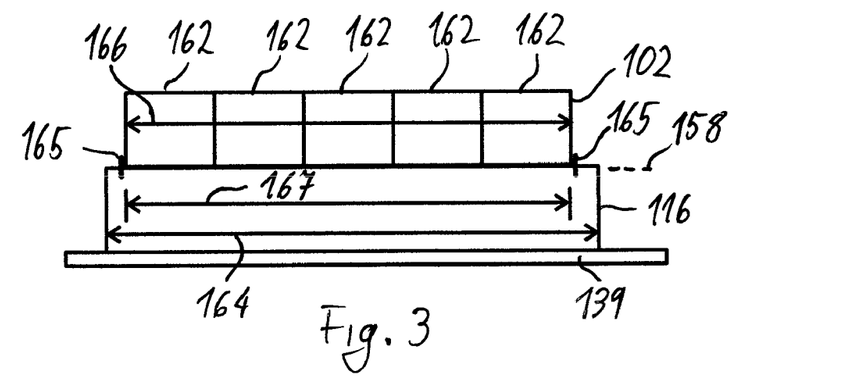
FIG. 3 shows a side view of an entire biogas plant according to embodiments of the herein disclosed subject matter.

FIG. 3 shows a side view of an entire biogas plant 100 according to embodiments of the herein disclosed subject matter.

In accordance with an embodiment a base plate 139 is provided, e.g. made of concrete. It is noted that generally herein the term "concrete" includes also "reinforced concrete". On the base plate 139 two supports 116, 216 are provided (of which one support 116 is visible in FIG. 3), e.g. in the form of concrete walls. According to an embodiment, the two supports 116, 216 run in parallel and are laterally spaced from each other so as to allow to build the fermentation container 102 between the two supports 116, 216. In accordance with an embodiment, the fermentation container 102 is made of steel. In accordance with a further embodiment, the fermentation container 102 is made of pieces 162 forming segments of the entire cross profile 112 of the fermentation container 102 (see FIG. 1, FIG. 2). According to an embodiment, the fermentation container 102 is an elongated container with a substantially rectangular layout. In accordance with an embodiment, the length 164 of the support 116 may or may not exceed the length 166 of the fermentation container. According to a further embodiment, the length 167 of the hinge extends over at least 80% of the entire length 166 of the fermentation container, e.g. over 100% of the length 166 of the fermentation container.

According to an embodiment, the location of the fermentation container 102 with respect to the support 116 is fixed in a direction along the pivot axis 158, e.g. by at least one stop element 165.

Figure 4:
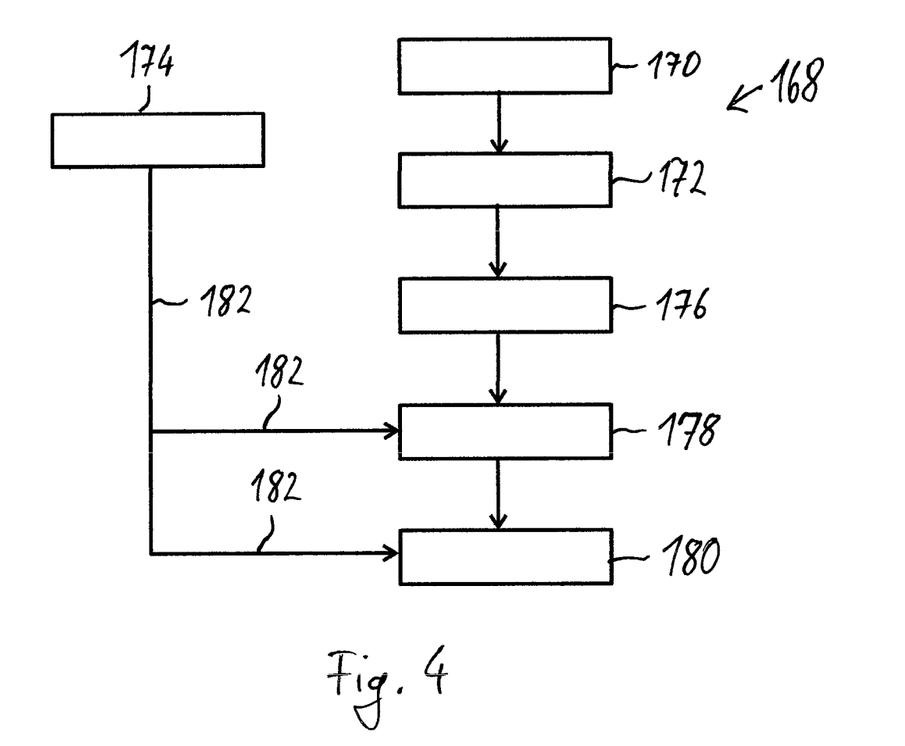
FIG. 4 illustrates a method of constructing a biogas plant comprising a fermentation container according to embodiments of the herein disclosed subject matter.

FIG. 4 illustrates a method 168 of constructing a biogas plant comprising a fermentation container according to embodiments of the herein disclosed subject matter.

According to an embodiment, a method disclosed herein may be performed in the order of the individual steps as presented herein. However, unless noted otherwise, a list of steps does not require the steps to be conducted in the listed sequence. Nevertheless, a list of steps is considered disclosing a method in which the steps are performed in the listed sequence.

In accordance with an embodiment, the construction method 168 starts with building the base plate 139, indicated at 170 in FIG. 4. Further, the method comprises building the supports 116, 216 on the base plate 139, indicated at 172 in FIG. 4. Further, the method comprises manufacturing of the pieces 162 of the fermentation container 102, indicated at 174 in FIG. 4. It should be noted that according to an embodiment the manufacturing of the pieces 162 is performed independently from the concrete construction 170, 172. According to an embodiment, the method further comprises attaching a position adjustment device to the support 116 and adjusting (e.g. leveling) an alignment part of the position adjustment device, indicated at 176 in FIG. 4. According to a further embodiment, the method further comprises attaching a first bearing part 130 to the alignment part of the position adjustment device, indicated at 178 in FIG. 4. According to a further embodiment, the method comprises positioning a connection part 126 of the fermentation container 102 on the first bearing part 130, indicated at 180 in FIG. 4. In accordance with an embodiment, the connection part 126 comprises a second bearing part 132 cooperating with the first bearing part 130. In accordance with an embodiment, the connection part 126 is a piece 162 of the fermentation container 102. According to a further embodiment, the method further comprises attaching further pieces 162 of the fermentation container 102 to the connection part 126, thereby building the entire fermentation container 102. Providing the pre-manufactured pieces 162 is indicated by arrows 182 in FIG. 4. The further pieces 162 of the fermentation container 102 may be attached to the connection part 126 (thereby forming e.g. a segment 163) before positioning the connection part 126 on the first bearing part 130.

As a result of the method 168, the fermentation container 102 is hingedly connected to the support 116, 216 via the first bearing part 130 and the second bearing part 132.

Embodiments of the herein disclosed method of construction have the advantage that the concrete construction is separated from the steel construction. This separation facilitates logistics since for example the concrete construction could be done by local firms whereas the steel construction could be pre-manufactured in pieces 162 by the manufacturer of the steel construction at its own premises, independently from the concrete construction. Embodiments of the herein disclosed subject matter (e.g. the position adjustment device) allow for an easy compensation of manufacturing tolerances of the concrete construction thus being relatively independent from the concrete construction.

In the following, further exemplary embodiment of the hinges 118, 218 are described.

Figure 5:
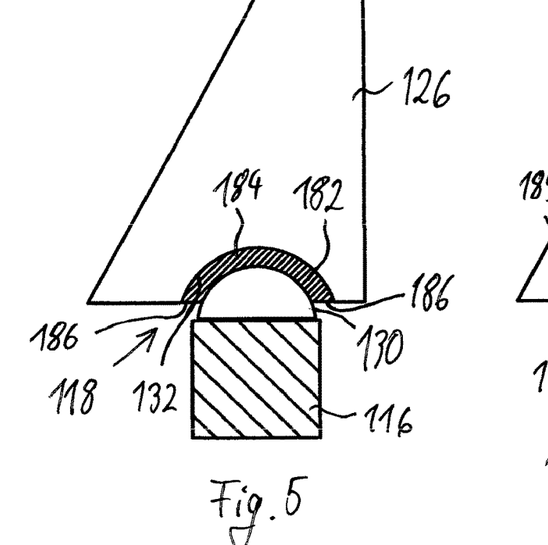
FIG. 5 shows a hinge according to embodiments of the herein disclosed subject matter.

FIG. 5 shows a hinge according to embodiments of the herein disclosed subject matter.

According to an embodiment, the hinge 118 comprises a slideway lining 182 between the first bearing part 130 and the second bearing part 132. The slideway lining 182 may reduce friction, may compensate unevenness of a surface of the first and/or second bearing part 130, 132, or may reduce thermal conductivity across the hinge 118. According to an embodiment, the slideway lining is made of a plastic material (.e. a polymer of high molecular weight (e.g. between 4 million gram/mol and 12 million gram/mol, e.g high molecular polyolefins such as high molecular polyethylene). According to an embodiment, the slideway lining 182 is subject to creep under the load of the weight of the fermentation container and its contents. Creep of the slideway lining 182 allows the slideway lining 182 to conform to the surfaces of the first and/or second bearing part 130, 132. Typical creep behavior of suitable polymers may be a strain below 1% (e.g. below 0.6%, such as below 0.5%) after applying a stress of 1 MPa for 10000 hours.

According to an embodiment, the hinge 118 comprises a lining chamber 184 which according to an embodiment is defined by the first bearing part 130, the second bearing part 132 and gap closing elements 186 which close the gap between the first bearing part 130 and the second bearing part 132, thereby closing the lining chamber 184. The closure of the lining chamber 184 is, according to an embodiment, at least sufficient to avoid creeping of the slideway lining 182 out of the lining chamber 184 during a predetermined time range, e.g. during the rated lifetime of the fermentation container, or, in another embodiment, during the rated lifetime of the slideway lining 182.

According to an embodiment the slideway lining 182 has an elastic modulus which is lower than the elastic modulus of the material from which the first bearing part 130 is formed and lower than the elastic modulus of the material from which the second bearing part 132 is formed. In other words, in such an embodiment the elastic deformation of the slideway lining 182 is higher than the elastic deformation of the first bearing part 130 and the second bearing part 132.

According to a further embodiment, the slideway lining 182 has a coefficient of thermal conduction which is lower than the coefficient of thermal conduction of the material from which the first bearing part 130 is formed and lower than the coefficient of thermal conduction of the material from which the second bearing part 132 is formed. In other words, by an appropriate choice of the material of the slideway lining, e.g. by using a polymer, the thermal conduction over the hinge 118 is reduced.

According to an embodiment, the second bearing part 132 may be provided at (e.g. attached to) a connection part 126 as disclosed herein.

Figure 6:
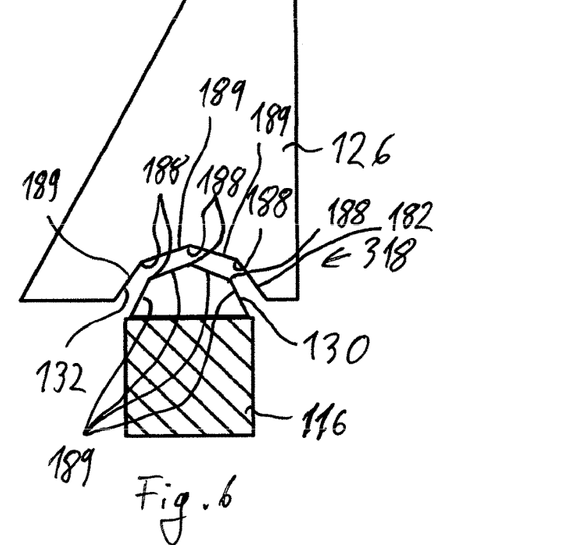
FIG. 6 shows a further hinge according to embodiments of the herein disclosed subject matter.

FIG. 6 shows a further hinge 318 according to embodiments of the herein disclosed subject matter.

In FIG. 6, the slideway lining is not shown in order to not obscure the features of the first bearing part 130 and the second bearing part 132. According to an embodiment, at least one of the first bearing part 130 and the second bearing part 132, e.g. both the first bearing part 130 and the second bearing part 132 have a segmented surface with a plurality of edges 188, as shown in FIG. 6. For example, according to an embodiment the first bearing part 130 and the second bearing part 132 are made of a polygonally bent sheet metal 189, or by a plurality of steel bars, extending parallel to the pivot axis (not shown in FIG. 6). According to an embodiment, the bars have a rectangular cross-section. Manufacturing the first bearing part 130 and the second bearing part 132 from a piece of sheet metal provides a cost efficient but nonetheless durable bearing part 130, 132.

Figure 7:
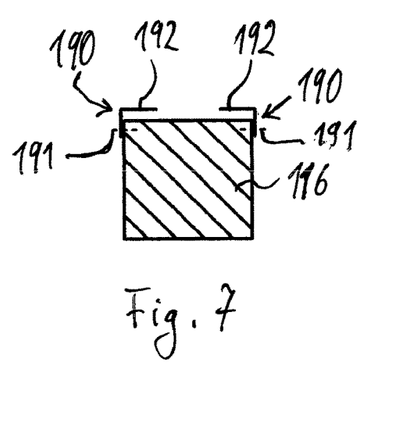
FIG. 7 shows a position adjustment device on a support according to embodiments of the herein disclosed subject matter.

FIG. 7 shows a position adjustment device 190 on a support 116 according to embodiments of the herein disclosed subject matter.

According to an embodiment, the position adjustment device 190 is attached to the support 116 prior to mounting the first bearing part 130 (not shown in FIG. 7) to the position adjustment device 190. According to an embodiment, the position adjustment device 190 comprises an alignment part 192 which is movably attached to the support 116 by a suitable attachment device, e.g. bolts, indicated at 191 in FIG. 7. According to an embodiment, the alignment part 192 is an elongated profile, e.g. a steel profile. According to an embodiment, the elongated profile has a cross-section in the shape of an L. Movability of the alignment part 192 with respect to the support 116 may be achieved e.g. by elongated holes (e.g. elongated in vertical direction) in the alignment part 192 through which the attachment devices 191 extend, or by other suitable means. Further, other possibilities of providing movability between two parts are known in the art and may also be implemented for providing movability of the alignment part 192 with respect to the support 116. By moving the alignment part 192 with respect to the support 116, the position and/or the alignment of the alignment part 192 with respect to the support 116 may be adjusted. In this manner, manufacturing tolerances of the support 116 may at least partially be overcome. According to an embodiment, two or more adjustment devices 190 may be provided per support 116, e.g. two adjustment devices 190 as shown in FIG. 7.

It is noted that any first bearing part 130 disclosed herein may be mounted to the support via a position adjustment device 190.

Figure 8:
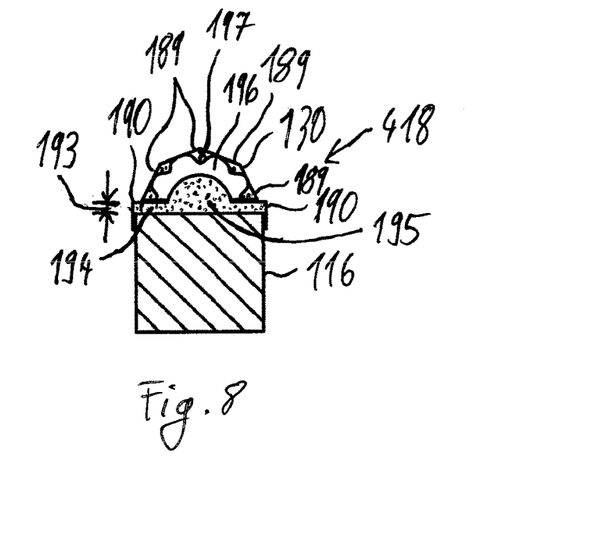
FIG. 8 shows in part a further hinge according to embodiments of the herein disclosed subject matter.

FIG. 8 shows in part a hinge 418 according to embodiments of the herein disclosed subject matter.

In accordance with an embodiment, a first bearing part 130 is mounted to support 116 via a position adjustment device 190. In accordance with an embodiment, the first bearing part 130 is spaced from the support by a distance 193. In accordance with a further embodiment, the space 194 between the first bearing part 130 and the support 116 is filled with a grouting material 195. The grouting material 195 assists in the transfer of forces between the first bearing part 130 and the support 116. In accordance with an embodiment, the first bearing part 130 is made from a piece of sheet metal, e.g. a polygonally shaped piece of sheet metal attached to a rib 196. In accordance with an embodiment, the rib 196 is shaped to provide a plurality of passages 197 between the rib 196 and the first bearing part 130. The plurality of passages 197 allow for a filling of the space 194 with the grouting material 195 without air bubbles. Air bubbles in the grouting material reduce the force transfer capabilities of the grouting material 195 and are therefore undesired. According to an embodiment, the position adjustment device 190 serves to adjust the position of the first bearing part 130, e.g. until the grouting material 195 is hardened. According to an embodiment, the position adjustment device 190 has no function after providing the grouting material 195.

Having regard to the subject matter disclosed herein, it should be mentioned that generally a biogas plant may be configured to include any combination of embodiments as disclosed herein. An example of such combinations are biogas plants shown in their entirety and in part in the drawings. Further, whenever a particular sequence of actions is provided herein, it should be understood that any different sequence may also be used as long as such a sequence is technically feasible.

It should be noted that any entity disclosed herein (e.g. component, element, piece, unit or device) is not limited to a dedicated entity as described in some embodiments. Rather, the herein disclosed subject matter may be implemented in various ways and with various granularity on device level or method level while still providing the specified functionality. Further, it should be noted that according to embodiments a separate entity (e.g. component, element, piece, unit or device) may be provided for each of the functions disclosed herein. According to other embodiments, an entity (e.g. component, element, piece, unit or device) is configured for providing two or more functions as disclosed herein. According to still other embodiments, two or more entities (e.g. components, elements, pieces, units or devices) are configured for providing together a function as disclosed herein.

It should be noted that the term "comprising" does not exclude other elements or steps, and that "a" or "an" does not exclude a plurality. Also elements described in association with different embodiments may be combined. It should also be noted that reference signs in the claims should not be construed as limiting the scope of the claims.

Further, it should be noted that while the exemplary examples in the drawings include a particular combination of several embodiments of the herein disclosed subject matter, any other combination of embodiment is also possible and is considered to be disclosed with this application.

In order to recapitulate some of the above described embodiments of the present invention one can state:

A biogas plant 100 is provided comprising a fermentation container 102 for receiving fermentation material 104 to be fermented. The fermentation container 102 comprises a lower wall part 108, 208 and an upper wall part 110, 210 wherein the upper wall part being positioned above the lower wall part 108, 208. Further, the biogas plant 100 comprises a support 116, 216 and a hinge 118, 218 wherein the hinge hingedly connects the fermentation container 102 to the support 116, 216 and wherein the hinge 118, 218 defines a pivot axis 158, 258 about which the upper wall part 110, 210 and the lower wall part 108, 208 are pivotable. According to an embodiment, two such supports 116, 216 e.g. made of concrete are provided and subsequently the fermentation container 102 is hingedly mounted thereon.

The invention claimed is:
1. A biogas plant comprising:
   a fermentation container for receiving fermentation material to be fermented, the fermentation container comprising a lower wall part and an upper wall part, the upper wall part being positioned above the lower wall part;
   a support;

a hinge, the hinge hingedly connecting the fermentation container to the support, the hinge defining a pivot axis about which the upper wall part and the lower wall part are pivotable;

the fermentation container comprising a lever;

the lever being connected to the lower wall part;

the lever being connected to the upper wall part;

the hinge comprising a first bearing part;

the hinge comprising a second bearing part at the lever, the second bearing part cooperating with the first bearing part and being moveable with respect to the first bearing part; and a grouting material in a space between the first bearing part and the support.

2. The biogas plant according to claim 1, the lower wall part being spaced from the pivot axis in a direction from the support towards the fermentation container; and/or the lower wall part exerting to the hinge a torque in a direction pivoting the upper wall part towards an interior of the fermentation container; and/or the lower wall part extending at an angle with regard to the direction of gravity.

3. The biogas plant according to claim 1, wherein in a filled state, a central part of a bottom of the fermentation container is vertically moveable.

4. The biogas plant according to claim 1, at least one of the first bearing part and the second bearing part having a segmented surface with a plurality of edges.

5. The biogas plant according to claim 1, the hinge further comprising:

a slideway lining between the first bearing part and the second bearing part, the slideway lining being made of a plastic material.

6. The biogas plant according to claim 5, the plastic material of the slideway lining being subject to creep; and the hinge further comprising a closed lining chamber comprising the slideway lining, the lining chamber being at least partially defined by the first bearing part and the second bearing part.

7. The biogas plant according to claim 5, the slideway lining having an elastic modulus which is lower than the elastic modulus of a bearing material from which at least one of the first bearing part and the second bearing part is formed.

8. The biogas plant according to claim 5, the slideway lining having a coefficient of thermal conduction which is lower than the coefficient of thermal conduction of a material from which the first bearing part is formed and lower than the coefficient of thermal conduction of a material from which the second bearing part is formed.

9. The biogas plant according to claim 1, further comprising:

a device configured for adjustment of a position of the first bearing part with respect to the support.

10. The biogas plant according to claim 1, the hinge extending over at least 80 percent of the entire length of the fermentation container.

11. The biogas plant according to claim 1, wherein the support is a wall extending lengthwise the fermentation container; and/or the location of the fermentation container with respect to the support is fixed in a direction along the pivot axis; and/or the fermentation container is made of metal.

12. The biogas plant according to claim 1, wherein the shape of the fermentation container is configured and the hinge is configured and located such that an increase of the level of fermentation material in the fermentation container reduces an outwardly directed force acting on the support in a direction away from the fermentation container.

13. The biogas plant according to claim 1, wherein the support is a first support, the hinge is a first hinge, the lower wall part is a first lower wall part, the upper wall part is a first upper wall part, and the pivot axis is a first pivot axis, the fermentation container further comprising:

a second lower wall part and a second upper wall part; and the biogas plant further comprising:

a second support spaced from the first support, the fermentation container being located between the first support and the second support;

a second hinge for hingedly connecting the fermentation container to the second support; and the second hinge defining a second pivot axis about which the second upper wall part and the second lower wall part are pivotable.

14. A method of constructing a biogas plant comprising a fermentation container being provided for receiving fermentation material to be fermented, the fermentation container comprising a lower wall part and an upper wall part being positioned above the lower wall part, the method, comprising:

providing a support;

hingedly connecting the fermentation container to the support by a hinge, the hinge defining a pivot axis about which the upper wall part and the lower wall part are pivotable;

the fermentation container comprising a lever;

connecting the lower wall part to the upper wall part with the lever;

the hinge comprising a first bearing part and a second bearing part at the lever, the second bearing part cooperating with the first bearing part and being moveable with respect to the first bearing part; and providing a grouting material in a space between the first bearing part and the support.

15. The method according to claim 14, wherein the hinge comprises a first bearing part and a second bearing part, the method comprising:

locating the first bearing part on the support;

adjusting a position of the first bearing part with respect to the support; and positioning the second bearing part on the first bearing part.

16. The method according to claim 15, wherein adjusting the position of the first bearing part with respect to the support comprises adjusting the vertical position of the first bearing part with respect to the support; and/or adjusting the position of the first bearing part with respect to the support comprises adjusting the horizontal position of the first bearing part with respect to the support.

17. The method according to claim 15, the method further comprising at least one of the following:

providing a bottom bearing which limits the downward movement of the central-lower part of the bottom of the fermentation container;

connecting pieces of the fermentation container to thereby generate a segment, the segment forming at least part of the entire cross profile of the fermentation container, the segment extending over a part of a length of the fermentation container;
mounting the segment to the bottom bearing and the first bearing part;
connecting the segment of the fermentation container with an adjacent segment to thereby build up the fermentation container.

18. The method according to claim 17, further comprising the order:
providing a base plate;
providing the support and the bottom bearing on the base plate;
providing the first bearing part on the support and providing the second bearing part on the segment;
mounting the segment to the first bearing part and the bottom bearing.

* * * * *